United States Patent [19]

Makris et al.

[11] Patent Number: 4,877,132
[45] Date of Patent: Oct. 31, 1989

[54] SYRINGE PROTECTION DEVICE

[76] Inventors: Luke Makris, 7455 Ridge Blvd., Chicago, Ill. 60645; George Dimopoulos, 916 Cumberland, Park Ridge, Ill. 60068

[21] Appl. No.: 326,099
[22] Filed: Mar. 20, 1989
[51] Int. Cl.⁴ .............................................. B65D 85/00
[52] U.S. Cl. ................................................... 206/364
[58] Field of Search ................ 206/364, 365, 366, 385

[56]  References Cited

U.S. PATENT DOCUMENTS

| 405,100 | 6/1889 | Kloppe | 206/364 X |
| 1,524,632 | 1/1925 | Pittenger | 206/365 |
| 1,711,594 | 5/1929 | Gillespie | 206/365 |
| 2,884,123 | 4/1959 | Dann et al. | 206/365 |
| 3,008,570 | 11/1961 | Roehr et al. | 206/364 X |
| 4,758,230 | 7/1988 | Rycroft | 206/366 X |

FOREIGN PATENT DOCUMENTS

| 696893 | 10/1940 | Fed. Rep. of Germany | 206/364 |
| 610245 | 6/1926 | France | 206/364 |
| 645024 | 6/1928 | France | 206/364 |
| 1408369 | 7/1965 | France | 206/364 |
| 336069 | 10/1930 | United Kingdom | 206/365 |

Primary Examiner—William Price

[57]  ABSTRACT

A syringe protection device has telescoping tubes with legs and surfaces compressively engaging syringe finger grips providing protection and economy.

17 Claims, 2 Drawing Sheets

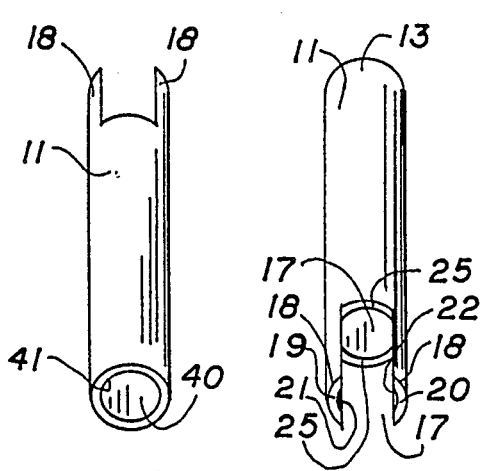
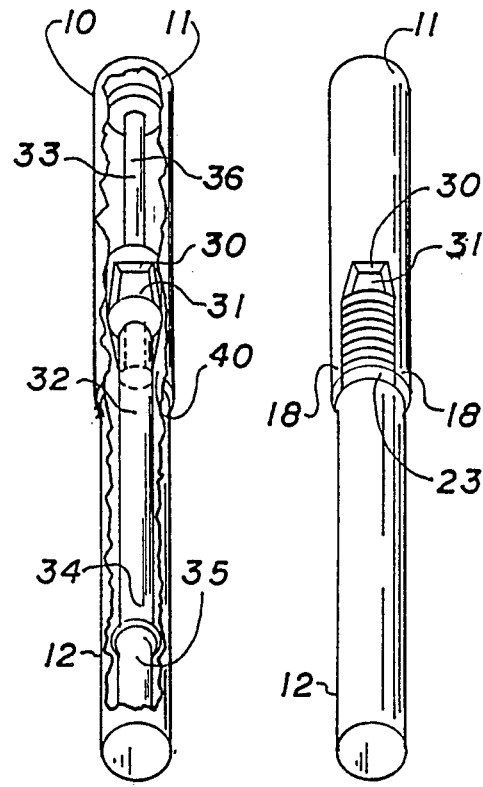
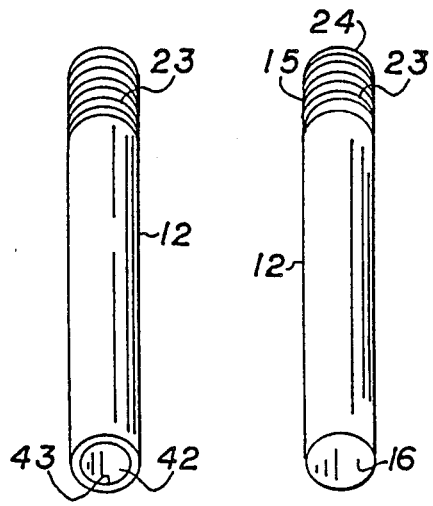
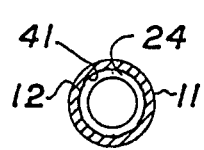
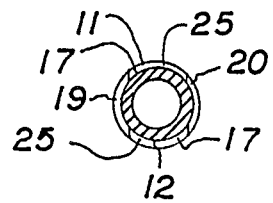
FIG. 6  FIG. 2  FIG. 3
FIG. 7  FIG. 1
FIG. 4  FIG. 5

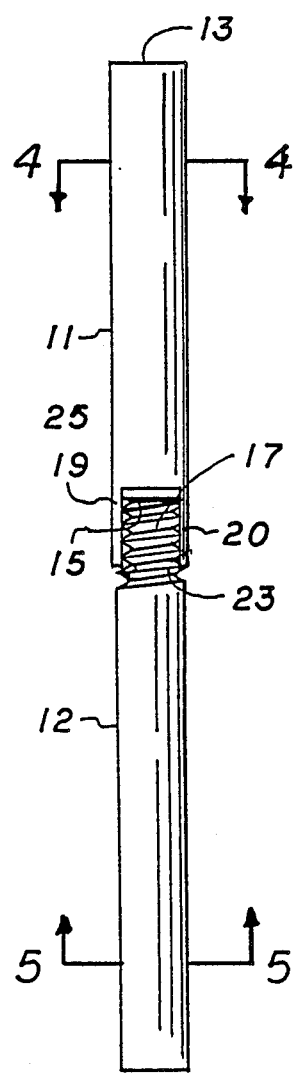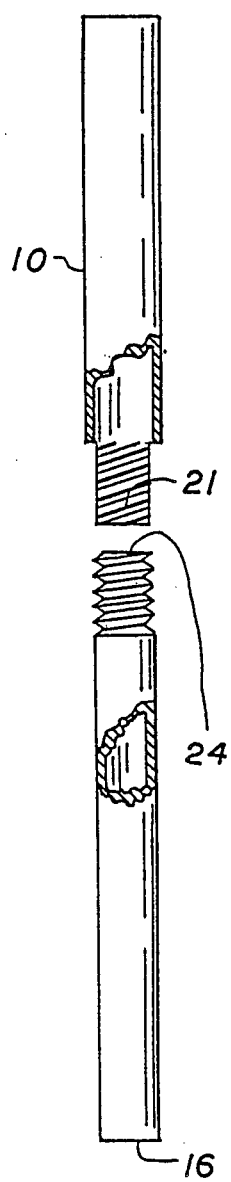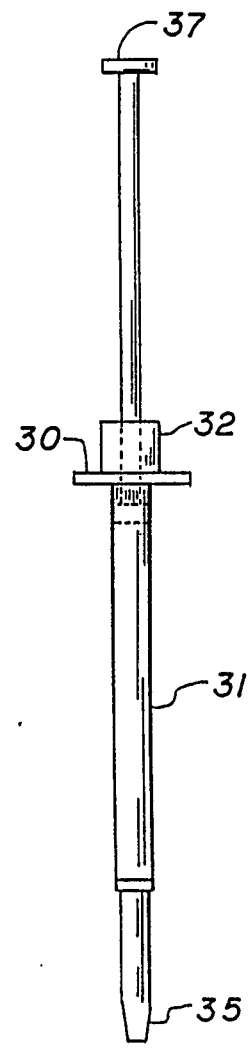
FIG. 8
FIG. 9
FIG. 10

SYRINGE PROTECTION DEVICE

BACKGROUND OF THE INVENTION

This invention provides a reusable container for protecting a medical syringe in a charged or uncharged condition. The container protects the syringe against accidental breakage, discharge or spoilage through exposure to light. The container also enhances protection offered by needle sheaths in reducing the likelihood of unwanted contact with a needle. The invention also provides for identification of the condition of charge in the syringe contained therein.

Prior art syringe protection devices are generally designed to meet three different objectives. The three purposes shown by prior art devices are: preserving sterility; tamper resistance or tamper evidence and reduction of unwanted contact with used syringes and needles. Prior art solutions sometimes combine two or three of these attributes. The prior art generally adopts a "use once and dispose" approach varying only to the extent the devices may be opened and locked closed once for destructive reopening under controlled conditions.

An example of a sterility preserving device is shown in Soren U.S. Pat. No. 3,157,277 which uses tear away seals. Multiple sealing media and collapsible members are also used in Thackston U.S. Pat. No. 3,820,652.

Various configurations of needle sheaths are used to cover needles on syringes in combination with breakaway elements. Typical of these approaches are Hamilton U.S. Pat. No. 3,367,488, Brown U.S. Pat. No. 3,783,997 and Vanderbeck U.S. Pat. No. 3,485,239. Other approaches are devices which retract the needles as shown in Armel U.S. Pat. No. 3,828,775 and Leeson U.S. Pat. No. 3,890,971.

Other needle sheath approaches include Staebler U.S. Pat. No. 4,742,910, Ogle U.S. Pat. No. 3,272,322, Brown U.S. Pat. No. 4,735,311 and Landis U.S. Pat. No. 4,664,259 and Smith U.S. Pat. No. 4,643,722. An additional tamper resistant structure is shown in Horner U.S. Pat. No. 4,671,408.

In certain situations there is a need to provide protection for charged and uncharged syringes with needles in place where the container, syringe and needle, either in combination or separately, can be reused. In these, the syringe itself, a separate needle sheath and the operator's procedures accomplish the object of sufficient sterility. In some situations there may be relatively low risk of infection from accidental contact, and adequate controls commensurate with risk of tampering are present. Under these circumstances a reusable device is desirable. One circumstance in particular is where an intervenes insulin user self-administered, prescribed insulin.

SUMMARY OF THE INVENTION

One advantage of the invention is that it protects a charged or uncharged syringe assembly complete with needle, body and plunger.

Another advantage of the invention is that it is reusable.

Another advantage of the invention is that photo sensitive spoilage is reduced.

Another advantage of the invention is that an indication of the charged and discharged position of the syringe plunger is provided.

Another advantage of the invention is that standardized syringes may be accommodated.

Another advantage of the invention is that presence or absence of a syringe in the container is indicated.

Another advantage of the invention is that it provides for compact storage of a syringe, and another advantage of the invention is that it provides for top and bottom orientation of a syringe in the container.

BRIEF DESCRIPTION OF THE DRAWINGS

FIG. 1 is a perspective view of the container.

FIG. 2 is a perspective cut away view of the container with a syringe therein.

FIG. 3 is an elevational views of the container.

FIG. 4 is a sectional view of the container taken substantially on line 4—4 of FIG. 8.

FIG. 5 is a sectional view of the container taken substantially on line 5—5 of FIG. 8.

FIG. 6 is a perspective view showing the top tube of the container in its open position.

FIG. 7 is a perspective view showing the bottom tube of the container in its open position.

FIG. 8 is an elevational view of the container in its closed position.

FIG. 9 is an elevational view of two parts of container.

FIG. 10 is an elevational view of a syringe.

DETAILED DESCRIPTION OF THE PREFERRED EMBODIMENT

FIG. 1 shows a syringe container having a top tube (11) and bottom tube (12). The top tube has a top end and a female opening receiving the bottom tube (12). The bottom tube has a male end (15) and a bottom end (16).

In the preferred embodiment a pair of slots (17) are provided in the walls (18) of the tube (11). Two elongate legs (19) and (20) extend from the tube (11) thereby defining the pair of slots (17) between them.

In the preferred embodiment the inner surface (21) and (22) of the elongate legs (19) and (20) are internally threaded to join with the bottom tube (12). Other alternative tube joining arrangements may be utilized such as adapting the legs (19) and (20) and male end of the bottom tube (12) to provide a bayonet fastening.

The joining between the top (11) and bottom (12) tubes is provided by external threads (23) on the male end (15) of the bottom tube (12). The end surface (24) of the bottom tube (12) abuts the finger grips of a syringe as will be shown in other Figures. The opposite surface of the finger grip in turn abuts the inner arcuate end surface (25) of each slot (17).

FIG. 2 is a cut away view of the container (10) with a syringe (31) contained therein. The syringe comprises a body (32) which has a plunger (33) in an opening at one end. Remote therefrom is the needle fitted to the opposite end (34). In this view the needle sheath (35) commonly supplied with the syringe (31) completely encases the needle carried at the needle end (34). The plunger (33) includes a shaft (36) and surface (37) for compressing the syringe assembly by applying pressure of thumb against the surface (37) while holding the body (31) by a pair of finger grips (30). Opposite the surface is a piston end (40) which exerts compression on the liquid contained in the syringe when the plunger is depressed.

The finger grips of the syringes are typically composed of a somewhat resilient material such as nylon or another plastic. Rotating the tube (11) and tube (12) relative to one another compresses the finger grip (30) between the surface (24) and surface (25). Rotation in the opposite direction releases the compression and permits disengagement of the two tubes (11) and (12).

FIG. 3 is a perspective view of the container (10) with its syringe (31) in place. Apparent in this view are the external (23) threads of the bottom (12) tube and the legs (18) of the top tube (11). In this view the syringe is present and the finger grip (30) compressed between surface (24) and the opposite surface on the top tube not visible in this view.

FIG. 4 is a sectional view looking along the axis of the container (10) from the top (13) at line 4—4 of FIG. 8. In this view the opening co-extensive with the interior (41) of the renders the surface (24) of the lower tube (12) visible.

FIG. 5 is a sectional view of the container (10) at line 5—5 of FIG. 8. The bottom end (16) of the bottom tube (12) is adapted with an opening (42). The top tube (11) has a larger diameter than the bottom tube (12) and is visible in this view. From the bottom the slots (17) are separated by the elongated legs (19) and (20). Also visible are the end surfaces of (25) of the slots (17).

Orientation of the syringe shown in FIG. 6 with its plunger at the top adapts the opening (40) as a viewing port to easily identify if the syringe has its plunger and surface, previously identified positioned to indicate a charged, or extended, position. Thus if the operator carries more than one syringe-container assembly he or she can easily determine whether one or the other is ready for use. In addition the opening being co-extensive with the interior surface (41) provides for ease of cleaning through manual or automatic means.

The opening (42) in the bottom tube (12) defined by the interior walls (43) as shown in FIG. 7 provides a visual indication of the presence of a syringe. This portion also verifies whether a syringe was placed in the container with a needle sheath thereon.

The presence of openings in the two tubes also permits ready cleaning by manual or automatic means.

FIG. 8 is a view of the respective ends of the tubes in their connected condition. The end (15) of tube (12) has the external threads (23) visible in this view. Visible with respect to the top tube (11) are the elongate legs (19) and (20) defining slots (17) between them. The slots (17) have end surfaces (25).

FIG. 9 shows a container (10) cut away to show internal threads (21). This view may be seen relative to the syringe (31) in FIG. 10. It is noted that the length of top tube (11) from the end (13) to the slot surfaces (25) in FIG. 9 relates to the distances from the finger grips (30) to plunger surface (37) of the extended plunger (35) in FIG. 10 in such a manner as to enclose the plunger completely in the top tube (11) as well as that portion of the body (32) which extends above the finger grips (30). The length of the bottom tube (12) from the inner surface (24) to the bottom end (16) in FIG. 9 is slightly greater than the distance from syringe finger grips (30) to the end of the needle sheath (35) in FIG. 10 such that the body and needle sheath of the syringe is completely enclosed in the tube (12). The interior diameter of the bottom tube is less than the diameter of the plunger surface (37) to prevent insertion of the plunger surface (37) in FIG. 10 in the tube (12) in FIG. 9 thereby preventing inversion of the syringe (31) relative to the container (10) which could otherwise result in the unwanted abutment of the longer body (31) and needle sheath (35) assembly with the end (13) of the top tube (11) or extension through the opening (40) in the embodiment shown in FIG. 6.

In accordance with my invention I claim:

1. A container for use with a syringe, having a body with two end portions one end portion adapted for fitting a needle and the other adapted for slidingly encompassing a plunger, the plunger having a syringe engagement end and a surface end, the syringe body having finger grip means, the improvement comprising;
    first tube means having a terminal end, an engagement end and interior and exterior surfaces;
    second tube means having a terminal end, an engagement end and interior and exterior surfaces;
    said first tube engagement end having finger grip engagement slots defined by elongate legs extending from said tube and engagement surface means disposed between said legs; and
    said legs having second tube engagement means;
    said second engagement end having first tube engagement means corresponding to the engagement means on the first tube and having a finger grip engagement surface;
    where said tubes may be engaged in telescoping relationship; and
    where said syringe is inserted in said container and said first tube engagement surfaces and second tube engagement surface bear against said syringe finger grips and are maintained in said bearing relation by the compression of the respective tube engagement means.

2. The invention according to claim 1, and
    said first tube adapted to completely enclose the syringe plunger in its charged condition; and
    the second tube adapted to completely enclose the needle end of the syringe including the needle and needle sheath contained thereon.

3. The invention according to claim 2, and
    said second tube means preventing inverted insertion of the syringe in the container.

4. The invention according to claim 3, and
    said first tube has a viewing port disposed at its terminal end for viewing the condition of the syringe contained therein.

5. The invention according to claim 4, and
    said second tube has a viewing port disposed at its terminal end for viewing the condition of the syringe contained therein.

6. A container for holding a medical syringe in charged or uncharged condition said syringe having a body with laterally extending resilient finger grips, a needle and a plunger having seal and thumb engagement ends, and adapted to carry a needle sheath comprising:
    a tube having medial and distal portions, the medial portion having means enabling opening of the tube for placement and removal of the syringe in charged or uncharged condition.
    said tube being openable into separate pieces, the pieces having gripping means for retaining the syringe in place, and
    said gripping means comprising opposed surfaces associated with each of the separate pieces of the opened tube, and in the interlocked position said surfaces embracing and compressing the finger grips of the syringe when in the interlocked position.

7. The invention according to claim 6, and said tube having orientation means for orienting the syringe therein,
the orientation means comprising internal dimension reducing means whereby the syringe body is permitted to pass into one portion of the container and the syringe plunger is prevented from passing into said portion.

8. The invention according to claim 7, and
the medial portion having syringe gripping means for resiliently holding the syringe in the tube, syringe presence indicator means for indicating whether the syringe is present in the tube and syringe orientation means for controlling orientation of the needle and plunger ends of the syringe in a predetermined relationship with said tube.

9. The invention according to claim 8, and
said opening means comprising two interlocking elements whereby in the closed position the elements interlock one another forming a single unit and in the open position said interlocking elements are released into separate pieces.

10. The invention according to claim 9, and
a first distal portion with charge state indicator means for indicating whether the syringe is in a charged or uncharged condition,
and comprising a viewing port in said distal portion of the tube.

11. The invention according to claim 10, and
the second distal portion having needle sheath indicator means for indicating whether or not a needle sheath is present on a syringe contained in the tube,
said needle sheath indicator means comprising a viewing part in the second distal portion of the tube.

12. For use with syringe having a body with a plunger extending from one end, a needle at the other end, said needle selectively enclosed by a needle sheath, and having laterally extending finger grips on the body, and a protective holder for containing said syringe in protective orientation therein, comprising:
a pair of tubular members adapted to be arranged in telescoping arrangement, at adjacent ends,
one of said members having axially extending open ended slots for receiving said finger grips therein,
means for threadily interconnecting said tubular members at said ends, said members engaging said finger grips therebetween for releasably interlocking same with said syringe, to hold said members from freely separately and to position said syringe in concentric relation with said holder.

13. The invention according to claim 12, and
said protective holder being repeatedly openable and closeable, and
said protective holder being opaque to limit light entry to the syringe.

14. the invention according to claim 13, and
said protective holder having syringe orientation means restricting the entry of the syringe plunger in the first one of the tubular members and permitting the entry of the syringe plunger in the second one of the tubular members,
the first tubular member adapted to accommodate the length of the body, needle and needle sheath, extending from the finger grip, and
the second tubular member adapted to accommodate the length of the extended plunger.

15. The invention according to claim 14, and
said protective holder having first indicator means for indicating the presence of a syringe body therein, by the operative positioning of the finger grips extending outwardly from the protective holder,
said first tubular member having second indicator means for indicating the presence of a needle sheath on the needle end of the syringe body, and
said second tubular member having third indicator means for indicating the charge position of the plunger extending from end of the syringe body.

16. A holder for a syringe comprising a pair of tubes adapted to be sleeved about opposite end portions of the syringe, and means for closing an intermediate portion of the syringe and securing the same to the holder and said tubes to each other,
said intermediate portion having two opposite finger grips extending perpendicular to the axis of the syringe,
said closing means comprising a pair of elongate legs on one of the tubes with two slots between them, a base surface at the end of each slot and a second base surface on the other tube,
threads on the respective tubes for engaging the tubes and compressing the finger grips between the base surfaces.

17. The invention according to claim 16, and
said tubes being provided with inspection means for determining the presence of a syringe and state of readiness for use of the syringe.

* * * * *